(12) United States Patent
Blattner et al.

(10) Patent No.: US 9,340,791 B2
(45) Date of Patent: May 17, 2016

(54) REDUCED GENOME BACTERIA WITH IMPROVED GENETIC STABILITY

(71) Applicant: SCARAB GENOMICS, LLC, Madison, WI (US)

(72) Inventors: Frederick R. Blattner, Madison, WI (US); Balint Csorgo, Szeged (HU); Gyorgy Posfai, Szeged (HU)

(73) Assignee: SCARAB GENOMICS, LLC, Madison, WI (US)

( * ) Notice: Subject to any disclaimer, the term of this patent is extended or adjusted under 35 U.S.C. 154(b) by 0 days.

(21) Appl. No.: 14/351,756

(22) PCT Filed: Oct. 19, 2012

(86) PCT No.: PCT/US2012/061027
§ 371 (c)(1),
(2) Date: Apr. 14, 2014

(87) PCT Pub. No.: WO2013/059595
PCT Pub. Date: Apr. 25, 2013

(65) Prior Publication Data
US 2014/0302555 A1    Oct. 9, 2014

Related U.S. Application Data

(60) Provisional application No. 61/549,375, filed on Oct. 20, 2011.

(51) Int. Cl.
| | | |
|---|---|---|
| *C12N 1/20* | (2006.01) | |
| *C12N 15/70* | (2006.01) | |
| *C12N 1/08* | (2006.01) | |
| *C12R 1/19* | (2006.01) | |
| *C12P 21/02* | (2006.01) | |
| *C12P 21/00* | (2006.01) | |
| *C07H 21/04* | (2006.01) | |

(52) U.S. Cl.
CPC ........ *C12N 15/70* (2013.01); *C12N 1/08* (2013.01); *C12N 1/20* (2013.01); *C12P 21/00* (2013.01); *C12P 21/02* (2013.01); *C12R 1/19* (2013.01)

(58) Field of Classification Search
None
See application file for complete search history.

(56) References Cited

U.S. PATENT DOCUMENTS

| | | | |
|---|---|---|---|
| 8,119,365 B2 * | 2/2012 | Blattner et al. | 435/69.1 |
| 2003/0138937 A1 | 7/2003 | Blattner | |
| 2009/0075333 A1 * | 3/2009 | Campbell et al. | 435/69.1 |

FOREIGN PATENT DOCUMENTS

WO    2007/024756 A2    3/2007

OTHER PUBLICATIONS

International Search Report of PCT/US2012/061027 dated Feb. 26, 2013.
Written Opinion of PCT/US2012/061027 dated Feb. 26, 2013.

* cited by examiner

*Primary Examiner* — Nancy T Vogel
(74) *Attorney, Agent, or Firm* — Morgan, Lewis & Bockius LLP

(57) ABSTRACT

Reduced genome bacteria with improved genetic stability are provided. Also provided are methods of producing polypeptides using the reduced genome bacteria with improved genetic stability.

15 Claims, 9 Drawing Sheets

```
                              SEQUENCE LISTING

<160> NUMBER OF SEQ ID NOS: 38

<210> SEQ ID NO 1
<211> LENGTH: 23
<212> TYPE: DNA
<213> ORGANISM: Artificial Sequence
<220> FEATURE:
<223> OTHER INFORMATION: polB-A PCR primer

<400> SEQUENCE: 1
ccgaattcag tatccaggcg agt                                              23

<210> SEQ ID NO 2
<211> LENGTH: 26
<212> TYPE: DNA
<213> ORGANISM: Artificial Sequence
<220> FEATURE:
<223> OTHER INFORMATION: polB-BR PCR primer

<400> SEQUENCE: 2
caggcaggtg tggcggaggg aatact                                           26

<210> SEQ ID NO 3
<211> LENGTH: 26
<212> TYPE: DNA
<213> ORGANISM: Artificial Sequence
<220> FEATURE:
<223> OTHER INFORMATION: polB-BF PCR primer

<400> SEQUENCE: 3
tccgccacac ctgcctgcgc cacgct                                           26

<210> SEQ ID NO 4
<211> LENGTH: 22
<212> TYPE: DNA
<213> ORGANISM: Artificial Sequence
<220> FEATURE:
<223> OTHER INFORMATION: polB-C PCR primer

<400> SEQUENCE: 4
ccggatccat tggcggcatt gt                                               22

<210> SEQ ID NO 5
<211> LENGTH: 19
<212> TYPE: DNA
```

```
<213> ORGANISM: Artificial Sequence
<220> FEATURE:
<223> OTHER INFORMATION: polB-D PCR primer

<400> SEQUENCE: 5
tgctgaacac cagtttgct                                              19

<210> SEQ ID NO 6
<211> LENGTH: 18
<212> TYPE: DNA
<213> ORGANISM: Artificial Sequence
<220> FEATURE:
<223> OTHER INFORMATION: polB-E PCR primer

<400> SEQUENCE: 6
aaccggtgaa gtggttga                                               18

<210> SEQ ID NO 7
<211> LENGTH: 24
<212> TYPE: DNA
<213> ORGANISM: Artificial Sequence
<220> FEATURE:
<223> OTHER INFORMATION: dinB-A PCR primer

<400> SEQUENCE: 7
ccggtaccgg gcataccgat gcga                                        24

<210> SEQ ID NO 8
<211> LENGTH: 30
<212> TYPE: DNA
<213> ORGANISM: Artificial Sequence
<220> FEATURE:
<223> OTHER INFORMATION: dinB-BR PCR primer

<400> SEQUENCE: 8
cagaatatac attgctcacc tctcaacact                                  30

<210> SEQ ID NO 9
<211> LENGTH: 29
<212> TYPE: DNA
<213> ORGANISM: Artificial Sequence
<220> FEATURE:
<223> OTHER INFORMATION: dinB-BF PCR primer

<400> SEQUENCE: 9
gaggtgagca atgtatattc tggtgtgca                                   29

<210> SEQ ID NO 10
<211> LENGTH: 24
<212> TYPE: DNA
<213> ORGANISM: Artificial Sequence
<220> FEATURE:
<223> OTHER INFORMATION: dinB-C PCR primer

<400> SEQUENCE: 10
ccggatccgc cgttaacgca tcaa                                        24

<210> SEQ ID NO 11
<211> LENGTH: 18
<212> TYPE: DNA
<213> ORGANISM: Artificial Sequence
<220> FEATURE:
<223> OTHER INFORMATION: dinB-D PCR primer

<400> SEQUENCE: 11
gtgttcgact cgctcgat                                               18
```

<210> SEQ ID NO 12
<211> LENGTH: 19
<212> TYPE: DNA
<213> ORGANISM: Artificial Sequence
<220> FEATURE:
<223> OTHER INFORMATION: dinB-E PCR primer

<400> SEQUENCE: 12
gagtcgtcgt agagtgcat                                                19

<210> SEQ ID NO 13
<211> LENGTH: 25
<212> TYPE: DNA
<213> ORGANISM: Artificial Sequence
<220> FEATURE:
<223> OTHER INFORMATION: umuDC-A PCR primer

<400> SEQUENCE: 13
ggaattcgga tgagcgtcgt cgcca                                         25

<210> SEQ ID NO 14
<211> LENGTH: 28
<212> TYPE: DNA
<213> ORGANISM: Artificial Sequence
<220> FEATURE:
<223> OTHER INFORMATION: umuDC-BR PCR primer

<400> SEQUENCE: 14
ttgagcgcaa caacagcagc gatgacaa                                      28

<210> SEQ ID NO 15
<211> LENGTH: 28
<212> TYPE: DNA
<213> ORGANISM: Artificial Sequence
<220> FEATURE:
<223> OTHER INFORMATION: umuDC-BF PCR primer

<400> SEQUENCE: 15
gctgctgttg ttgcgctcaa tgaacctt                                      28

<210> SEQ ID NO 16
<211> LENGTH: 25
<212> TYPE: DNA
<213> ORGANISM: Artificial Sequence
<220> FEATURE:
<223> OTHER INFORMATION: umuDC-C PCR primer

<400> SEQUENCE: 16
gctgcagatc gcttacctga ttgtc                                         25

<210> SEQ ID NO 17
<211> LENGTH: 18
<212> TYPE: DNA
<213> ORGANISM: Artificial Sequence
<220> FEATURE:
<223> OTHER INFORMATION: umuDC-D PCR primer

<400> SEQUENCE: 17
aatgctccat ctgcggtt                                                 18

<210> SEQ ID NO 18
<211> LENGTH: 18
<212> TYPE: DNA
<213> ORGANISM: Artificial Sequence
<220> FEATURE:

<223> OTHER INFORMATION: umuDC-E PCR primer

<400> SEQUENCE: 18
gctctatcct tcgccgtt                                          18

<210> SEQ ID NO 19
<211> LENGTH: 21
<212> TYPE: DNA
<213> ORGANISM: Artificial Sequence
<220> FEATURE:
<223> OTHER INFORMATION: lexA-A PCR primer

<400> SEQUENCE: 19
gttatggtcg cattttggat a                                      21

<210> SEQ ID NO 20
<211> LENGTH: 32
<212> TYPE: DNA
<213> ORGANISM: Artificial Sequence
<220> FEATURE:
<223> OTHER INFORMATION: lexA-BR PCR primer

<400> SEQUENCE: 20
gatatctttc atcgccatcc cgctgacgcg ca                          32

<210> SEQ ID NO 21
<211> LENGTH: 24
<212> TYPE: DNA
<213> ORGANISM: Artificial Sequence
<220> FEATURE:
<223> OTHER INFORMATION: lexA-BF PCR primer

<400> SEQUENCE: 21
ggatggcgat gaaagatatc ggca                                   24

<210> SEQ ID NO 22
<211> LENGTH: 23
<212> TYPE: DNA
<213> ORGANISM: Artificial Sequence
<220> FEATURE:
<223> OTHER INFORMATION: lexA-C PCR primer

<400> SEQUENCE: 22
ccggatccca gcaacggaac ggt                                    23

<210> SEQ ID NO 23
<211> LENGTH: 18
<212> TYPE: DNA
<213> ORGANISM: Artificial Sequence
<220> FEATURE:
<223> OTHER INFORMATION: lexA-D PCR primer

<400> SEQUENCE: 23
cggtgctgat tgccatta                                          18

<210> SEQ ID NO 24
<211> LENGTH: 18
<212> TYPE: DNA
<213> ORGANISM: Artificial Sequence
<220> FEATURE:
<223> OTHER INFORMATION: lexA-E PCR primer

<400> SEQUENCE: 24
gggctatcaa gatgacca                                          18

-continued

```
<210> SEQ ID NO 25
<211> LENGTH: 24
<212> TYPE: DNA
<213> ORGANISM: Artificial Sequence
<220> FEATURE:
<223> OTHER INFORMATION: recA-D PCR primer

<400> SEQUENCE: 25
cggctagcga cgggatgttg attc                                           24

<210> SEQ ID NO 26
<211> LENGTH: 18
<212> TYPE: DNA
<213> ORGANISM: Artificial Sequence
<220> FEATURE:
<223> OTHER INFORMATION: recA-E PCR primer

<400> SEQUENCE: 26
gtgctgatta tgccgtgt                                                  18

<210> SEQ ID NO 27
<211> LENGTH: 24
<212> TYPE: DNA
<213> ORGANISM: Artificial Sequence
<220> FEATURE:
<223> OTHER INFORMATION: BMD30-A PCR primer

<400> SEQUENCE: 27
ccgaattcag tccgcacgca actt                                           24

<210> SEQ ID NO 28
<211> LENGTH: 28
<212> TYPE: DNA
<213> ORGANISM: Artificial Sequence
<220> FEATURE:
<223> OTHER INFORMATION: BMD30-BR PCR primer

<400> SEQUENCE: 28
ctcgccttaa tttacatact tttggtgc                                       28

<210> SEQ ID NO 29
<211> LENGTH: 27
<212> TYPE: DNA
<213> ORGANISM: Artificial Sequence
<220> FEATURE:
<223> OTHER INFORMATION: BMD30-BF PCR primer

<400> SEQUENCE: 29
tatgtaaatt aaggcgagat tattaaa                                        27

<210> SEQ ID NO 30
<211> LENGTH: 24
<212> TYPE: DNA
<213> ORGANISM: Artificial Sequence
<220> FEATURE:
<223> OTHER INFORMATION: BMD30-C PCR primer

<400> SEQUENCE: 30
ccggatccac atggcgcgtt acaa                                           24

<210> SEQ ID NO 31
<211> LENGTH: 18
<212> TYPE: DNA
<213> ORGANISM: Artificial Sequence
<220> FEATURE:
<223> OTHER INFORMATION: BMD30-D PCR primer
```

```
<400> SEQUENCE: 31
tgataccgcc gcacaaca                                                    18

<210> SEQ ID NO 32
<211> LENGTH: 18
<212> TYPE: DNA
<213> ORGANISM: Artificial Sequence
<220> FEATURE:
<223> OTHER INFORMATION: BMD30-E PCR primer

<400> SEQUENCE: 32
actggtgtgt ctcgcaag                                                    18

<210> SEQ ID NO 33
<211> LENGTH: 18
<212> TYPE: DNA
<213> ORGANISM: Artificial Sequence
<220> FEATURE:
<223> OTHER INFORMATION: cycA-D PCR primer

<400> SEQUENCE: 33
ctgatgccgg taggttct                                                    18

<210> SEQ ID NO 34
<211> LENGTH: 18
<212> TYPE: DNA
<213> ORGANISM: Artificial Sequence
<220> FEATURE:
<223> OTHER INFORMATION: cycA-E PCR primer

<400> SEQUENCE: 34
gcgccatcca gcatgata                                                    18

<210> SEQ ID NO 35
<211> LENGTH: 19
<212> TYPE: DNA
<213> ORGANISM: Artificial Sequence
<220> FEATURE:
<223> OTHER INFORMATION: AK54-D PCR primer

<400> SEQUENCE: 35
atgataatga atgacatca                                                   19

<210> SEQ ID NO 36
<211> LENGTH: 24
<212> TYPE: DNA
<213> ORGANISM: Artificial Sequence
<220> FEATURE:
<223> OTHER INFORMATION: AK55-E PCR primer

<400> SEQUENCE: 36
ctcgagttag accaactctc caaa                                             24

<210> SEQ ID NO 37
<211> LENGTH: 18
<212> TYPE: DNA
<213> ORGANISM: Artificial Sequence
<220> FEATURE:
<223> OTHER INFORMATION: Sce2 PCR primer

<400> SEQUENCE: 37
attaccctgt tatccta                                                     18

<210> SEQ ID NO 38
<211> LENGTH: 20
```

```
<212> TYPE: DNA
<213> ORGANISM: Artificial Sequence
<220> FEATURE:
<223> OTHER INFORMATION: T7 PCR primer

<400> SEQUENCE: 38
taatacgact cactataggg                                              20
```

REDUCED GENOME BACTERIA WITH IMPROVED GENETIC STABILITY

This application is the 371 U.S. national stage of International Application Number PCT/US2012/061027 filed Oct. 19, 2012 and claims the benefit under 35 U.S.C. 119(e) of U.S. Provisional Application No. 61/549,375 filed Oct. 20, 2011, the entire contents of each of which are hereby incorporated by reference.

SEQUENCE LISTING SUBMISSION VIA EFS-WEB

A computer readable text file, entitled "010447-5034-US-sequence-listing_ST25.txt", created on or about Apr. 13, 2014, with a file size of about 8 KB contains the sequence listing for this application and is hereby incorporated by reference in its entirety.

FIELD OF THE INVENTION

The present invention is directed to reduced genome bacteria having a very low mutation rate and methods of using the reduced genome bacteria. The reduced genome bacteria are particularly useful for high fidelity maintenance of nucleic acids and stable expression of genes that have proved difficult to clone in bacterial hosts.

BACKGROUND OF THE INVENTION

Intrinsic mechanisms for generating diversity are important for survival of bacterial populations in the dynamically changing environmental conditions present in nature. However, in the controlled environment of the laboratory, these mechanisms can lead to unwanted genotypic and phenotypic alterations and the spontaneous genetic modification of an established production strain or a clone library is generally highly undesirable.

*Escherichia coli* (*E. coli*) is a universal cloning host and is the most common organism used in the production of proteins, metabolites and secondary metabolites in both research and industry. Several modifications have been made to improve the performance of *E. coli* hosts in these settings all of which follow the basic principle of streamlining metabolic pathways for the increased production of a given biomaterial coupled with reduction of unwanted byproducts. Along these lines, a variety of nonessential genes have been removed from an *E. coli* background to form viable reduced genome *E. coli* strains with little or no significant reduction in growth.

Although these reduced genome bacteria have proved beneficial in many respects, some genes, in their functional forms, remain difficult or impossible to clone in bacterial vectors even in reduced genome bacteria. Accordingly, there is a need for stable bacterial hosts with very low mutation rates in which such genes could be cloned.

SUMMARY OF THE INVENTION

The present invention provides a reduced genome bacterium wherein the gene(s) encoding at least one of the three error-prone DNA polymerases, Pol II, PolIV and PolV, are non-functional. In a preferred embodiment, the genes encoding Pol II and PolIV are non-functional and the gene encoding PolV is functional or non-functional. In a particularly preferred embodiment, none of these genes is functional in the reduced genome bacteria. The genes may be rendered non-functional by deletion of the genes in part or in whole from the genome of the bacteria or may be rendered non-functional by disrupting the genes.

In one embodiment, the genome of the reduced genome bacterium has a genome that is genetically engineered to be from about 5% to about 30% smaller than the genome of its native parent strain and lacks all insertion sequences. Reduced genome bacteria may be produced by deleting selected genes from a native parental strain of a bacterium or may, for example, be entirely synthesized as an assembly of preselected genes. As is readily apparent from the discussion herein, a reduced genome bacterium has fewer than the full complement of genes found in a native parent strain to which it is compared, and with which it shares certain essential genes.

Methods for producing a polypeptide employing the reduced genome bacteria are also provided. In one embodiment, the polypeptide is produced by culturing reduced genome bacteria having one or more non-functional genes selected from the group consisting of the genes encoding Pol II, PolIV and PolV and further comprising a nucleic acid encoding the polypeptide operatively linked to an expression control sequence, under conditions suitable for expression of the polypeptide. In a related embodiment, the nucleic acid encodes a "toxic" polypeptide which is difficult or impossible to clone in bacteria having functional PolII, PolIV and PolV genes.

These and other embodiments of the present invention are described in more detail herein below.

DETAILED DESCRIPTION OF THE INVENTION

Figure 1:
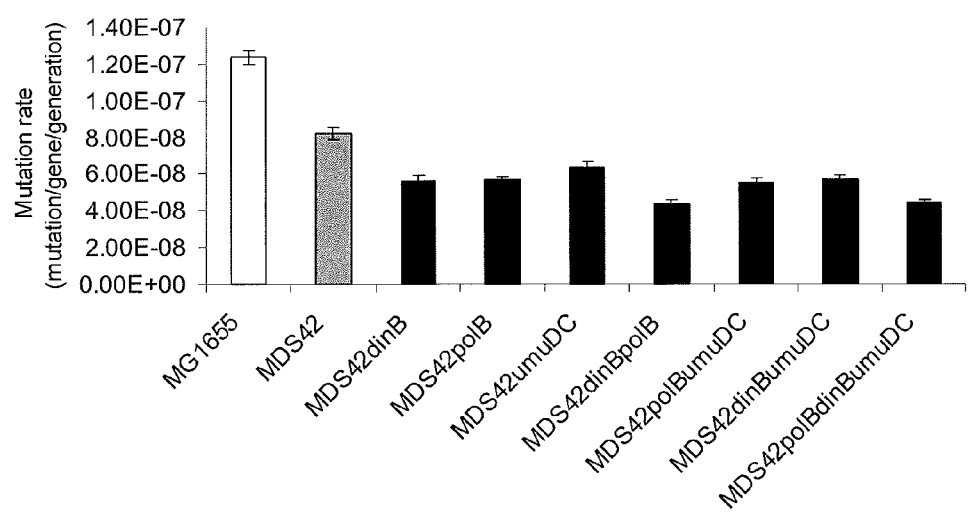
FIG. 1 illustrates the spontaneous mutation rates of reduced genome bacteria (MDS42) with non-functional (deletions in this case) dinB, polB, and umuDC genes, separately and in every possible combination as compared with MDS42 and MG1655 controls. Mutation rates were determined by a fluctuation analysis on mutations occurring in cycA. The decrease in mutation rate between wild-type MG1655 to MDS42 is due to the absence of insertion events, while the further decrease from MDS42 to the different error-prone polymerase mutants is due to a lower point-mutation rate. Values are averages of 4 independent measurements

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the pertinent art at issue. Also, the disclosure of ranges is intended as a continuous range including every value between the minimum and maximum values recited as well as any ranges that can be formed by such values. This includes ranges that can be formed that do or do not include a finite upper and/or lower boundary. This also includes ratios that are derivable by dividing a given disclosed numeral into another disclosed numeral. Accordingly, the skilled person will appreciate that many such ratios, ranges, and ranges of ratios can be unambiguously derived from the data and numbers presented herein and all represent various embodiments of the present invention.

The term "reduced genome bacterium" herein means a bacterium having about 1% to about 75% of its genome (e.g. protein coding genes) deleted, for example about 5%, about 10%, about 20%, about 30% about 40%, about 50% or about 60% of the genome deleted. In one embodiment, the reduced genome bacteria used in the practice of the present invention have a genome that is preferably genetically engineered to be at least two percent (2%) and up to twenty percent (20%) (including any number therebetween) smaller than the genome of a native parent strain. Preferably, the genome is at least five percent (5%) and up to thirty percent (30%) smaller than the genome of a native parent strain. More preferably, the genome is eight percent (8%) to fourteen percent (14%) to twenty percent (20%) (including any number therebetween) or more smaller than the genome of the native parent strain. Alternatively, the genome may be engineered to be less than 20%, less than 30%, less than 40% or less than 50% smaller than the genome of a native parental strain. The term "native parental strain" means a bacterial strain found in a natural or native environment as commonly understood by the scientific community and on whose genome a series of deletions can be made to generate a bacterial strain with a smaller genome. Native parent strain also refers to a strain against which the engineered strain is compared and wherein the engineered strain has less than the full complement of the native parent strain. The percentage by which a genome has become smaller after a series of deletions is calculated by dividing "the total number of base pairs deleted after all of the deletions" by "the total number of base pairs in the genome before all of the deletions" and then multiplying by 100. Similarly, the percentage by which the genome is smaller than the native parent strain is calculated by dividing the total number of nucleotides in the strain with the smaller genome (regardless of the process by which it was produced) by the total number of nucleotides in a native parent strain and then multiplying by 100

In one embodiment, the term "reduced genome bacteria" refers to bacteria for which removal of the above amounts of genome does not unacceptably affect the ability of the organism to grow on minimal medium. Whether removal of two or more genes "unacceptably affects" the ability of the organism to grow on minimal medium in the present context depends on the specific application. For example, a 30% reduction in proliferation rate may be acceptable for one application but not another. In addition, adverse effect of deleting a DNA sequence from the genome may be reduced by measures such as changing culture conditions. Such measures may turn an otherwise unacceptable adverse effect to an acceptable one. In one embodiment, the proliferation rate is approximately the same as the parental strain. However, proliferation rates ranging from about 5%, 10%, 15%, 20%, 30%, 40% to about 50% lower than that of the parental strain are within the scope of the invention. More particularly, doubling times of bacteria of the present invention may range from about five minutes to about three hours. Non-limiting examples of suitable reduced genome bacteria, as well as methods for deleting DNA from a bacterium such as E. coli, are disclosed in U.S. Pat. Nos. 6,989,265 and 7,303,906, U.S. Pat. Pub. Nos. 20060270043, 2006/0199257 and 2007/0054358 and WIPO Pub. No. WO 2003/070880, each of which is hereby incorporated by reference herein.

In several embodiments, a reduced genome bacterium is provided having at least one non-functional gene selected from the group consisting of the gene(s) encoding DNA Polymerase II, DNA Polymerase IV and DNA Polymerase V. Reduced genome bacteria in which one or more of these genes are non-functional exhibit a substantial improvement in genetic stability compared to bacteria having the same genetic background but in which these genes are functional. In one aspect, the gene(s) are rendered non-functional by deletion, for example by the "scarless" deletion methods described at column 8, line 45 to column 14, line 41 of U.S. Pat. No. 6,989,265. These methods result in a precise deletion of the target gene with no inserted DNA resulting from the deletion process (i.e. "scarless" deletions) and are therefore the preferred deletion methods. It is to be understood, however, that any method of deleting target genes, in whole or in part, known in the art may be employed to render one or more of the genes encoding DNA Polymerase II, DNA Polymerase IV and DNA Polymerase V non-functional. Alternatively, one or more of the genes encoding DNA Polymerase II, DNA Polymerase IV and DNA Polymerase V may be rendered non-functional by disrupting the gene(s) by using any technique known in the art. For example, the target gene(s) may disrupted by replacing the gene with a non-functional allele by homologous recombination. Disruption and deletion may be used in combination to produce any combination of non-functional genes encoding DNA Polymerase II, DNA Polymerase IV and DNA Polymerase V in the bacterium.

In one embodiment, any one of the genes encoding DNA Polymerase II, IV and V may be rendered non-functional and the remaining two genes may be functional. In other embodiments, any combination of two of the genes encoding DNA Polymerase II, IV and V may be rendered non-functional in the reduced genome bacteria and the remaining gene may be functional. For example, the genes encoding DNA Polymerase II and IV may be rendered non-functional and the gene encoding DNA Polymerase V may be functional. Alternatively, the genes encoding DNA Polymerase II and V may be rendered non-functional and the gene encoding DNA Polymerase IV may be functional. Alternatively, the genes encoding DNA polymerase IV and V may be rendered non-functional and the gene encoding DNA Polymerase II may be functional. In a preferred embodiment, the genes encoding DNA Polymerase II and DNA Polymerase IV are non-functional in the reduced genome bacterium and the gene encoding DNA Polymerase V is either functional or non-functional. In a particularly preferred embodiment, the genes encoding DNA Polymerase II, DNA Polymerase IV and DNA Polymerase V are all non-functional in the reduced genome bacterium.

In another preferred embodiment, the reduced genome bacterium with one or more non-functional gene selected from the group consisting of the gene(s) encoding DNA Polymerase II, DNA Polymerase IV and DNA Polymerase V has a genome that is genetically engineered to be at least five percent (5%) and up to thirty percent (30%) (including any number therebetween) smaller than the genome of a native parent strain. In another preferred embodiment, the reduced genome bacterium has a genome that is between 4.41 Mb and 3.71 Mb, between 4.41 Mb and 3.25 Mb or between 4.41 Mb and 2.78 Mb.

The parent of the reduced genome bacterium of the invention may be any bacterial strain. In a preferred embodiment, the parent of the reduced genome bacterium of the invention is an *E. coli* strain, such as an *E. coli* K-12 or B strain. *E. coli* K12 strains include derivative strains such as MG1655, W3110, DH1, DH10B, DH5α, Invα, Top10, Top10F, JM103, JM105, JM109, MC1061, MC4100, XL1-Blue, EC100, BW2952, or EC300. *E. coli* B strains include REL606, BL/R and BL21(DE3).

The nucleotide sequence of the genome of the parental strain may be partially or completely known. The complete genomic sequence of several *E. coli* and other commonly used laboratory microorganisms is known (see e.g. Blattner et al., Science, 277:1453-74 (1997); GenBank Accession No. U00096; NCBI database, Accession No. AP009048, Perna et al., Nature, 409, 529-533 (2001); Hayashi et al., DNA Res., 8, 11-22 (2001); Welch et al., Proc. Natl. Acad. Sci., USA 99:17020-17024 (2002), GenBank Accession No. AE014075, EMBL Accession No. CP000948, EMBL Accession No. CP001637, EMBL Accession No. CP001396, EMBL Accession No. CP000819, and EMBL Accession No. CP001509, each of which is incorporated herein by reference).

In a preferred embodiment, the parent of the reduced genome bacterium of the invention is *E. coli* strain K12 MG1655 (annotated version m56), (NCBI accession no. U000961) with a genome having 4,639,674 base pairs. In another preferred embodiment, the parent of the reduced genome bacterium is *E. coli* strain BL21(DE3) (EMBL accession no. CP001509) with a genome having 4,557,508 base pairs. The coordinates of the genes encoding DNA Polymerase II (polB), DNA Polymerase IV (dinB) and DNA Polymerase V (umuDC) in the *E. coli* K12 MG1655 genome are provided at Table 1.

TABLE 1

| Gene | Coordinates |
|---|---|
| polB (b0060) | 63429-65780 |
| dinB (b0231) | 250898-251953 |
| umuDC (b1183-b1184) | 1229990-1231677 |

In a particularly preferred embodiment, a reduced genome *E. coli* bacterium is provided having a genome between five percent (5%) and thirty percent (30%) smaller than the genome of a native parent strain and lacking all insertion sequence (IS) elements and having at least one non-functional gene selected from the group consisting of the gene(s) encoding DNA Polymerase II, DNA Polymerase IV and DNA Polymerase V. Positions of the IS elements on a genome map of *E. coli* MG1655 (annotated version 54) are shown in FIG. 1 and Table 2 of U.S. Patent Publication No. 2003/138937, the contents of which are incorporated herein by reference. Insertion sequence elements which commonly occur in *E. coli* and which may be removed, include without limitation, IS1, IS2, IS3, IS4, IS5, IS30, IS150, IS186, IS600, IS911 and IS10. In a particularly preferred embodiment, a reduced genome *E. coli* is provided lacking all insertion sequences and having non-functional polB and dinB genes and even more preferably having non-functional polB, dinB and umuDC genes.

In a related embodiment, the reduced genome bacterium is an *E. coli* bacterium lacking at least the following genes (identified by "b" numbers based on the designations set out in Blattner et al., Science, 277:1453-74 and in GenBank Accession No. 400096): b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153 and b2945 and also having one or more non-functional genes selected from polB, dinB and umuDC. In a particularly preferred embodiment, polB and dinB are non-functional and even more preferably polB, dinB and umuDC are all non-functional. The reduced genome *E. coli* bacterium may be strain MDS42, the genome of which lacks all insertion sequences, with one or more non-functional polB, dinB and umuDC genes, preferably with non-functional polB and dinB genes and even more preferably with all three genes non-functional. The reduced genome may also be strain MDS43 or MDS66 (or any derivative strain), with one or more non-functional polB, dinB and umuDC genes, preferably with all three genes non-functional.

Various protein coding genes can be deleted to form reduced genome bacteria. In *E. coli* and other bacteria, a type of DNA sequence that can be deleted includes those that in general will adversely affect the stability of the organism or of the gene products of that organism. Such elements that give rise to instability include without limitation transposable elements, insertion sequences, and other "selfish DNA" elements which may play a role in genome instability. For example, insertion sequence (IS) elements and their associated transposes are often found in bacterial genomes, and thus are targets for deletion. IS sequences are common in *E. coli*, and all of them may be deleted. For purposes of clarity in this document, we use the term IS element and transposable element generically to refer to DNA elements, whether intact or defective, that can move from one point to another in the genome. An example of the detrimental effects of IS elements in science and technology is the fact that they can hop from the genome of the host *E. coli* into a BAC plasmid during propagation for sequencing. This artifact can be prevented by deletion from the host cells of all IS elements. For a specific application, other specific genes associated with genomic instability, such as active and inactive prophages may also be deleted.

Reduced genome bacteria of the invention may also be engineered to lack, for example, without limitation, certain genes unnecessary for growth and metabolism of the bacteria, pseudogenes, prophage, undesirable endogenous restriction-modification genes, pathogenicity genes, toxin genes, fimbrial genes, periplasmic protein genes, invasin genes, lipopolysaccharide genes, class III secretion systems, phage virulence determinants, phage receptors, pathogenicity islands, RHS elements, sequences of unknown function and sequences not found in common between two strains of the same native parental species of bacterium. Other DNA sequences that are not required for cell survival can also be deleted or omitted.

The reduced genome bacteria of the invention may comprise a heterologous nucleic acid encoding a polypeptide. The polypeptide may be a therapeutic protein such as insulin, an interleukin, a cytokine, a growth hormone, a growth factor, erythropoietin, a colony stimulating factor, interferon, or an antibody. The heterologous nucleic acid may be placed within a vector such as a plasmid and operatively linked to a promoter and optionally additional regulatory sequences.

Reduced genome bacteria having one or more non-functional polB, dinB and umuDC genes, preferably with at least non-functional polB and dinB genes, and further lacking all insertion sequences exhibit surprising genetic stability that enables the cloning of toxic nucleic acids which are difficult or impossible to isolate or maintain even in reduced genome bacteria lacking all insertion sequences. A "toxic" nucleic acid may be a nucleic acid which, when propagated in a host strain, results in an elevated mutation rate. A toxic nucleic acid may also result in an elevated rate of IS element transposition. An elevated rate of mutation of a toxic nucleic acid may be determined by comparison to a host strain propagating a control nucleic acid.

The reduced genome bacteria comprising one or more non-functional polB, dinB and umuDC genes may be used to produce polypeptides. Briefly a bacterium of the invention comprising a heterologous nucleic acid encoding a polypeptide operatively linked to an expression control sequence, as described above, may be incubated under conditions sufficient to allow expression of the polypeptide product.

Overexpression of even a well-tolerated protein of interest may lead to elevated IS transposition rates and activate the stress response of the cell leading to significantly increased mutation rates. Plasmids encoding the protein of interest rapidly acquire loss-of-function mutations under these conditions and bacteria carrying these mutated plasmids quickly take become dominant in the culture due at least in part to the growth inhibitory effect of intact plasmids encoding the overexpressed protein. Bacteria of the invention, which exhibit a surprising genomic stability and fidelity, delay the appearance of such mutant plasmids and the cells can produce the functional toxic protein for an extended period of time.

Recombinant proteins may be expressed in the periplasm or cytoplasm. The expression of proteins in the periplasm is routinely used for industrial use and has been reviewed in Hanahan, J. Mol. Biol., 166:557-580 (1983); Hockney, Trends Biotechnol., 12:456-632 (1994); and Hannig et al., Trends Biotechnol., 16:54-60 (1998), each of which is incorporated herein by reference. Recombinant proteins may be produced in the periplasm by expressing fusion proteins in which they are attached to a signal peptide that causes secretion into the periplasmic space. There, the signal peptide may be cleaved off by specific signal peptidases. The protein transported into the periplasmic space may be biologically active.

The recombinant protein may be co-expressed with chaperones/disulfide-bond forming enzymes, which may provide proper folding of the recombinant protein. Nucleic acid sequences of such proteins useful for periplasmic expression of recombinant protein include, without limitation, those described in U.S. Pat. Nos. 5,747,662; 5,578,464 and 6,022,952, each of which is incorporated herein by reference.

EXAMPLE 1

Production of Reduced Genome *E. coli*

Reduced genome strain MDS39 was produced as described in International Patent Publication No. WO 2003/070880, which is incorporated herein by reference. Briefly, a series of reduced genome strains (MDS01-MDS39) were produced by making a series of 39 cumulative deletions (approximately 14.1% of the genome) of nucleic acid sequences from the parental strain *E. coli* MG1655.

Hybridization to genome scanning chips (NimbleGen Systems, Madison, Wis.) containing the K-12 sequence and all sequences in the IS database revealed that MDS39, the first strain designed to lack all IS elements, unexpectedly contained additional copies of an IS element that had hopped to new locations during its production. These IS elements were deleted to produce MDS40. The fhuACDB (the tonA locus) was deleted from MDS40 to produce MDS41. The location and function of each cumulative deletion made to produce MDS01-MDS41 can be found at Table 2 of U.S. Application Publication No. 2007/0054358, the entire content of which is incorporated herein by reference. The endA gene was then deleted from MDS41 to produce MDS42.

The genes coding for DNA polymerase II (polB), DNA polymerase IV (dinB) and DNA polymerase V (umuDC) were deleted from the genome of MDS42 in a scarless manner using a suicide plasmid-based method as described in U.S.

Pat. No. 6,989,265 and Feher et al., Methods Mol. Biol., 416:251-259 (2008) with plasmids pST76-A and pSTKST. Gene deletions were made individually and also joined in all possible combinations to produce the following strains: MDS42polB, MDS42dinB, MDS42umuDC, MDS42polBdinB, MDS42polBumuDC, MDS42dinBumuDC and MDS42polBdinBumuDC. Individual deletions were combined by P1 phage transduction of the marked (with integrated suicide-plasmids) intermediates of the deletion constructs, followed by endonuclease cleavage-stimulated out-recombination and loss of the plasmid. All deletions were verified by polymerase chain reaction (PCR) and sequencing using flanking primers. Primer sequences used in the study are listed at Table 2:

TABLE 2

| Primer Name | Sequence (5'-3') | Application |
|---|---|---|
| polB-A | ccgaattcagtatccaggcgagt (SEQ ID NO: 1) | deletion of polB |
| polB-BR | caggcaggtgtggcggagggaatact (SEQ ID NO: 2) | deletion of polB |
| polB-BF | tccgccacacctgcctgcgccacgct (SEQ ID NO: 3) | deletion of polB |
| polB-C | ccggatccattggcggcattgt (SEQ ID NO: 4) | deletion of polB |
| polB-D | tgctgaacaccagtttgct (SEQ ID NO: 5) | deletion of polB |
| polB-E | aaccggtgaagtggttga (SEQ ID NO: 6) | deletion of polB |
| dinB-A | ccggtaccgggcataccgatgcga (SEQ ID NO: 7) | deletion of dinB |
| dinB-BR | cagaatatacattgctcacctctcaacact (SEQ ID NO: 8) | deletion of dinB |
| dinB-BF | gaggtgagcaatgtatattctggtgtgca (SEQ ID NO: 9) | deletion of dinB |
| dinB-C | ccggatccgccgttaacgcatcaa (SEQ ID NO: 10) | deletion of dinB |
| dinB-D | gtgttcgactcgctcgat (SEQ ID NO: 11) | deletion of dinB |
| dinB-E | gagtcgtcgtagagtgcat (SEQ ID NO: 12) | deletion of dinB |
| umuDC-A | ggaattcggatgagcgtcgtcgcca (SEQ ID NO: 13) | deletion of umuDC |
| umuDC-BR | ttgagcgcaacaacagcagcgatgacaa (SEQ ID NO: 14) | deletion of umuDC |
| umuDC-BF | gctgctgttgttgcgctcaatgaacctt (SEQ ID NO: 15) | deletion of umuDC |
| umuDC-C | gctgcagatcgcttacctgattgtc (SEQ ID NO: 16) | deletion of umuDC |
| umuDC-D | aatgctccatctgcggtt (SEQ ID NO: 17) | deletion of umuDC |
| umuDC-E | gctctatccttcgccgtt (SEQ ID NO: 18) | deletion of umuDC |
| lexA-A | gttatggtcgcattttggata (SEQ ID NO: 19) | modification of lexA |
| lexA-BR | gatatctttcatcgCcatcccgct gacgcgca (SEQ ID NO: 20) | modification of lexA |
| lexA-BF | ggatgGcgatgaaagatatcggca (SEQ ID NO: 21) | modification of lexA |
| lexA-C | ccggatcccagcaacggaacggt (SEQ ID NO: 22) | modification of lexA |

TABLE 2-continued

| Primer Name | Sequence (5'-3') | Application |
|---|---|---|
| lexA-D | cggtgctgattgccatta (SEQ ID NO: 23) | modification of lexA |
| lexA-E | gggctatcaagatgacca (SEQ ID NO: 24) | modification of lexA |
| recA-D | cggctagcgacgggatgttgattc (SEQ ID NO: 25) | deletion of recA |
| recA-E | gtgctgattatgccgtgt (SEQ ID NO: 26) | deletion of recA |
| BMD30-A | ccgaattcagtccgcacgcaactt (SEQ ID NO: 27) | deletion of mcrBC |
| BMD30-BR | ctcgccttaatttacatacttttggtgc (SEQ ID NO: 28) | deletion of mcrBC |
| BMD30-BF | tatgtaaattaaggcgagattattaaa (SEQ ID NO: 29) | deletion of mcrBC |
| BMD30-C | ccggatccacatggcgcgttacaa (SEQ ID NO: 30) | deletion of mcrBC |
| BMD30-D | tgataccgccgcacaaca (SEQ ID NO: 31) | deletion of mcrBC |
| BMD30-E | actggtgtgtctcgcaag (SEQ ID NO: 32) | deletion of mcrBC |
| cycA-D | ctgatgccggtaggttct (SEQ ID NO: 33) | analysis of cycA mutations |
| cycA-E | gcgccatccagcatgata (SEQ ID NO: 34) | analysis of cycA mutations |
| AK54-D | atgataatgaatgacatca (SEQ ID NO: 35) | sequencing of sinI |
| AK55-E | ctcgagttagaccaactctccaaa (SEQ ID NO: 36) | sequencing of sinI |
| Sce2 | attaccctgttatcccta (SEQ ID NO: 37) | pST76 sequencing primer |
| T7 | taatacgactcactataggg (SEQ ID NO: 38) | pST76 sequencing primer |

Primers marked with A, C, BF, and BR were used to create homology regions by recombinant PCR for genomic integration of the suicide plasmids. Primers marked with D or E were homologous to flanking genomic regions, and were used for checking the deletions/allele replacements by PCR and sequencing. Capital letters in lexA primers indicate the point mutation introduced in the gene.

EXAMPLE 2

Spontaneous Mutation Rates in Reduced Genome *E. coli*

The spontaneous mutation rate of each strain was then determined using a D-cycloserine resistance assay, detecting all types of mutations in the cycA gene, as described in Feher et al., Mutat. Res. 595(1-2):184-190 (2006). Briefly, in a fluctuation assay, 20 tubes of 1 ml MS medium (as described in Hall, Mol. Biol. Evol., 15(1):1-5 (1998)) supplemented with 0.2% glucose were inoculated with approximately $10^4$ cells each, and cultures were grown to early stationary phase. Aliquots of 50 µl from each tube were then spread on MS plates containing D-cycloserine (0.04 mM). The estimated number of mutations per tube (m) was calculated from the number of colonies by using the Ma-Sandri-Sarkar maximum likelihood method (Sarkar et al., Genetica, 85(2):173-179 (1992)). Equation 41 from Stewart et al., Genetics, 124(1):175-185 (1990) was used to extrapolate the obtained m value, valid for 50 µl to 1 ml. Statistical comparisons of m values were made only when the difference in total cell number was negligible (<3%, P≤0.6, with a two-tailed, unpaired t test). The total number of cells in a tube was calculated by spreading dilutions from three random tubes onto nonselective plates. Dividing the number of mutations per tube by the average total number of cells in a tube gave the mutation rate (mutation/cell/generation).

The deletion of each gene by itself results in at least a 20% decrease in mutation rate measured by this method (all values significant, P<0.05, two-tailed, unpaired t test). The results are graphically depicted at FIG. 1. Combining the different deletions decreased the mutation rate decreased further, with the lowest mutation rates being that of MDS42polBdinB and the triple deletion strain MDS42polBdinBumuDC. The effect of combining the polB and dinB deletions is multiplicative, indicating an independent mode of action for these polymerases. The deletion of umuDC generated no additional decrease of the mutation rate when any of the other two error prone polymerases were missing, possibly marking an interaction among the genes or their products. Compared to the parent MDS42 strain, strains MDS42polBdinB and MDS42polBdinBumuDC showed a nearly 50% reduction in spontaneous mutation rate ($8.2 \times 10^{-8}$ mutation/cell/generation decreased to $4.34 \times 10^{-8}$ and $4.45 \times 10^{-8}$ respectively).

To verify that the absence of genes encoding DNA polymerase II, IV and V has no adverse effect on fitness, growth rates of the different strains were measured in MOPS minimal medium. Ten parallel cultures originating from 10 individual colonies for each strain were picked and grown in a Bioscreen C instrument. Growth curves were measured by following the optical densities (O.D.) at 540 nm of each culture. None of the deletions had a significant effect on fitness in MOPS minimal medium, even when combined in the triple deletion strain MDS42polbdinBumuDC.

Figure 2:
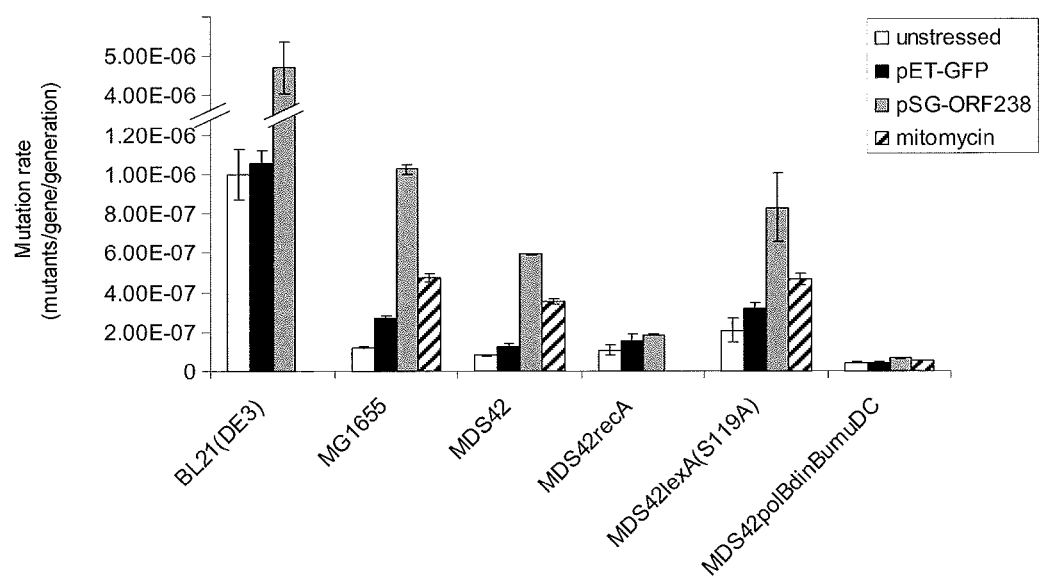
FIG. 2 illustrates the effect of different stresses on the mutation rate of various strains. The effect of stress imposed by overproduction of green fluorescent protein (GFP), overproduction of a toxic peptide from pSG-ORF238, and treatment with mitomycin C are shown. All measurements were made using the cycA fluctuation assay, values are averages of 3 independent measurements each. BL21(DE3) and MDS42recA failed to grow in the presence of 0.1 µg/ml mitomycin C.

To determine whether upstream inactivation of the entire SOS response via regulator mutants would have the same effects on the spontaneous mutation rate as elimination of the genes encoding DNA polymerase II, IV and V, MDS42recA and MDS42lexA were created. MDS42recA comprises a scarless deletion of recA (coordinates 2820783-2821861 of MG1655), the product of which is required for induction of the autoproteolysis of LexA. MDS42lexA comprises a replacement of the lexA gene with a non-functional allele in which the serine at position 119 is replaced with alanine (S119A). Each of these genes (recA and lexA) is required in order to de-repress the SOS regulon genes. Accordingly, neither MDS42recA nor MDS42lexA is able to induce the SOS pathway. None of these modifications had an adverse effect on the overall fitness of the strains, as measured by growth rates of the strains in MOPS minimal medium as described above. Surprisingly, neither strain showed a significant decrease in spontaneous mutation rate when compared to MDS42. In the case of MDS42lexA, a slight increase was actually observed ($2.07 \times 10^{-7}$ compared to $8.2 \times 10^{-8}$ of MDS42). The results are illustrated at FIG. 2 (blank bars (unstressed)).

EXAMPLE 3

Stress-Induced Mutation Rates in Reduced Genome E. coli

The mutation rates of MDS42recA, MDS42lexA and MDS42polbdinBumuDC under stressful conditions were then measured and compared.

Mitomycin-C, a DNA cross-linking agent that causes lesions in double stranded DNA, directly activates the SOS response, leading to up-regulation of DNA polymerases II, IV and V. A sub-inhibitory concentration (0.1 µg/ml) of mitomycin-C was used to stress the cells and the effect on mutation rates was analyzed. The results are illustrated at FIG. 2 (hatched bars (mitomycin))

Protein overproduction imposes stress on the host cell. The effect of overproduction of a benign protein, Green Fluorescent Protein (GFP), on mutation rates was tested. The gene encoding GFP was cloned on a plasmid as an inducible construct controlled by a T7 promoter. To express the GFP, T7 RNA polymerase encoding variants of strains MDS42polBdinBumuDC (MDS42polBdinBumuDC-T7), MDS42recA (MDS42recA-T7), and MDS42lexA (MDS42lexA-T7) were constructed by replacing the yahA-yaiL genomic region with an IPTG-inducible lac operator/T7 polymerase cassette. T7 RNA polymerase encoding variants of MDS42 (MDS42-T7), MG1655 (MG1655-T7), and the widely used protein production strain BL21(DE3) were also constructed and the effects of overexpression of GFP on mutation rate in each strain was measured and compared. The results are illustrated at FIG. 2 (solid black bars (pET-GFP)).

Next, the effect of overproduction of a toxic protein (ORF238, a small, leucine-rich hydrophobic protein) on mutation rates in the bacteria was tested by transforming the strains with plasmid pSG-ORF238, an IPTG-inducible, pSG1144-based construct capable of overproducing the ORF238 protein. The results are illustrated at FIG. 2 (shaded bars (pSG-ORF238)). Overproduction of ORF238 significantly increased the mutation rate of MDS42. The values for MDS42polBdinBumuDC remained stable under the same conditions.

The results demonstrate that, with the exception of MDS42recA and MDS42polBdinBumuDC, the various stresses increased the mutation rate of all strains including MDS42. Overproduction of the toxic ORF238 protein had the largest effect: a greater than 5-fold increase in mutation rate was measured. Sub-inhibitory concentration of mitomycin-C caused a greater than 2-3-fold increase in the mutation rate and BL21(DE3) and MDS42recA were unable to grow under these conditions. Overproduction of GFP had a relatively minor effect, resulting in a 1.5 to 2-fold increase in mutation rates.

In contrast, no significant increase in mutation rate in the presence of any of the stressors could be seen in either MDS42recA or MDS42polBdinBumuDC. Interestingly, MDS42lexA did not follow this behavior—the strain showed an increase in mutation rate in response to all of the stresses. MDS42polBdinBumuDC can be characterized as the genetically most stable strain, displaying the lowest spontaneous mutation rate and showing negligible response to stressful conditions.

Figure 3:
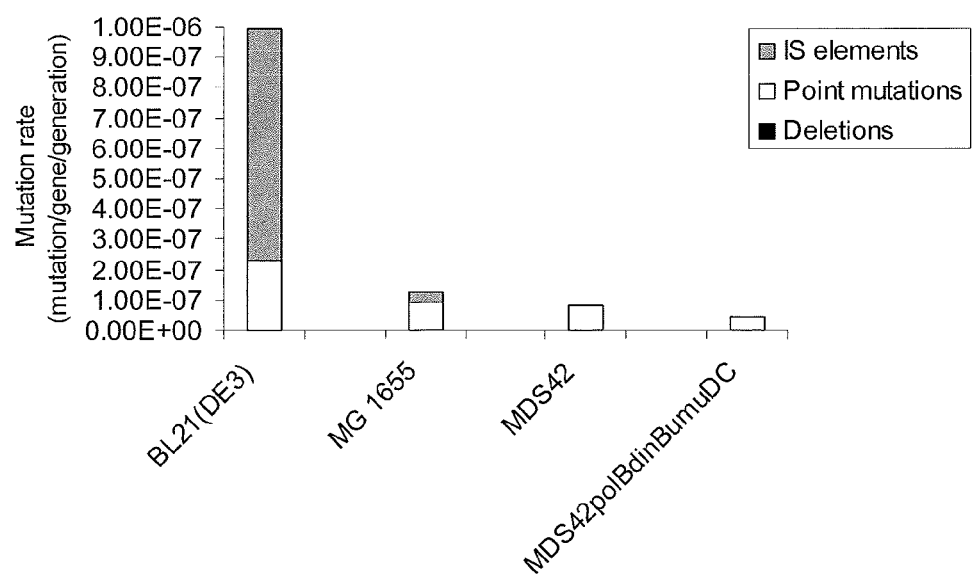
FIG. 3 illustrates a comparison of the mutational spectra of various strains. The bar graph shows the distribution of cycA mutation types, detected by polymerase chain reaction (PCR) analysis. The share of deletions in MG1655, MDS42, and MDS42polBdinBumuDC is too low to be visible, and no deletions were detected in BL21(DE3).

The most commonly used protein production strain, BL21 (DE3), displayed a mutation rate nearly two orders of magnitude higher than MDS42polBdinBumuDC when overproducing the toxic ORF238 protein. To analyze this difference, mutation spectra of BL21(DE3), MG1655, MDS42 and MDS42polBdinBumuDC were studied by PCR analysis of cycA in cycloserine-resistant mutants. Briefly, a 1,877-bp genomic segment encompassing the entire gene was amplified from mutant cells using the primer pair cycA1-D/cycA2-E. A representative sample was obtained by analyzing 5 colonies from each parallel plate, yielding a total of 96 samples per experiment. The amplified fragments were resolved on an agarose gel and compared to a fragment generated from the wild-type template. Identical sizes indicated a mutation affecting only one or a few nucleotides, a decrease in size or failure of amplification indicated a deletion, and a detectable size increase indicated in IS insertion. The results are illustrated at FIG. 3. In MG1655, 74% of the mutations proved to be point mutations, 24% were IS insertions, and 2% were deletions. In contrast, in BL21(DE3), 77% of cycA mutations were IS insertions. Although the proportion of point mutations in BL21(DE3) was much smaller (74% in MG1655 versus 23% in BL21(DE3)), the actual rate of point mutations was significantly higher in BL21(DE3) ($2.28 \times 10^{-7}$ compared to $9.2 \times 10^{-8}$ in MG1655). No deletions were found among the cycA alleles in BL21(DE3).

Figure 4:
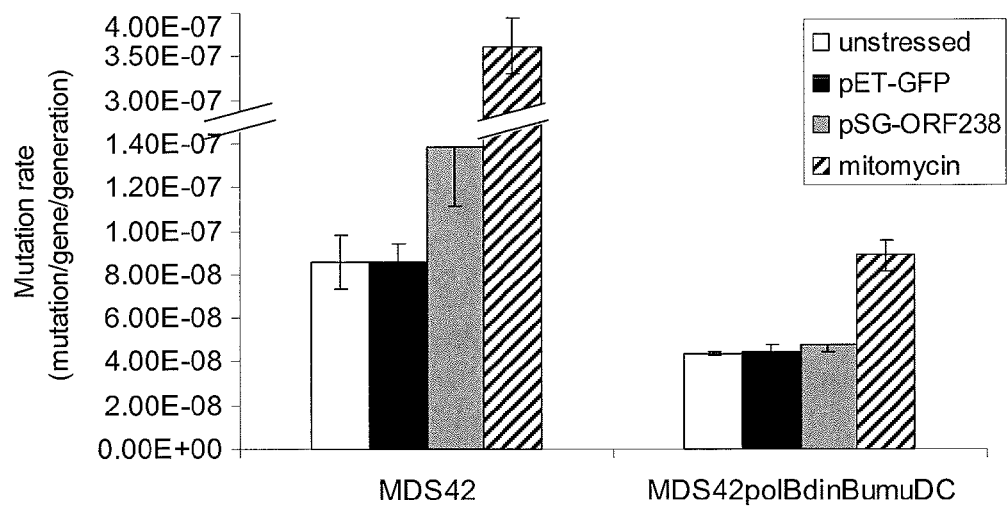
FIG. 4 illustrates the mutation rate of MDS42 and MDS42polBdinBumuDC measured by a rifampicin resistance assay. Values are averages of 3 independent measurements each.

To confirm the data obtained using the cycA fluctuation assay, mutation rates of MDS42 and MDS42polBdinBumuDC under each of the different stress conditions were also measured using the rifampicin resistance assay. This assay detects point mutations in the essential rpoB gene, as described in Jin and Gross, J. Mol. Biol., 202(1):45-58 (1988). Briefly, twenty tubes of 1 ml LB were inoculated with $10^4$ cells each, and cultures grown to early stationary phase. Appropriate dilutions were spread onto non-selective LB agar plates and LB agar plates containing rifampicin (100 µg/ml). Colony counts were performed after 24 or 48 hours, respectively. Mutation frequencies were reported as a proportion of the number of rifampicin-resistant colonies relative to the total viable count. The results correspond to the mean value obtained in three independent experiments for each strain and condition. When required, different stress conditions were provided in the same manner as in the cycA assay. The data obtained using the rifampicin resistance assay were consistent with the cycA fluctuation data, as illustrated at FIG. 4. MDS42polBdinBumuDC had a significantly lower spontaneous mutation frequency compared to MDS42. In response to the overproduction of the toxic ORF238 protein, as well as in the presence of mitomycin-C, the mutation rate of MDS42 became significantly elevated, while the response of MDS42polBdinBumuDC was much less substantial.

EXAMPLE 4

MDS42polBdinBumuDC Provides Improved Stability to a Toxic Protein-Expressing Plasmid To demonstrate the surprising advantage of reduced genome bacteria comprising non-functional polB, dinB and/or umuDC genes, a plasmid-based mutation screen was designed. Plasmid pSin32 carries an inducible copy of sinI, coding for the SinI methyltransferase of *Salmonella enterica* serovar Infantis, cloned into the XhoI site of the pET3-His plasmid. SinI methylates the inner cytosines in DNA at GG(A/T)CC sites, producing 5-methylcytosine, thereby creating targets for the McrBC endonuclease, which cleaves DNA containing methylcytosine. A plasmid carrying methylated SinI sites (e.g. pSin32, self-methylated at its 8 SinI sites), therefore cannot establish itself in a mcrBC$^+$ host. When introduced into mcrBC$^-$ hosts, the plasmid is methylated when expression of sinI is induced, but can be maintained.

The mcrBC gene was deleted during production of MDS42 and accordingly all MDS42 strains are mcrBC. The mcrBC gene was deleted from BL21(DE3) to create strain BL21(DE3)mcrBC. Plasmid pSin32 was electroporated into MDS42-T7, MDS42polBdinBumuDC-T7 and BL21(DE3)mcrBC. After 1 hour of recovery incubation at 37° C. in 1 ml LB, 100 µl of the transformed cultures were placed in 100 ml LB supplemented with ampicillin (Ap) and incubated at 37° C. From the remaining 900 µl, plasmid DNA was isolated according to standard protocols. After 7 hours of incubation, the cultures reached O.D.$_{540}$=~0.2, at which point the samples were induced with IPTG (1 mM final concentration). Samples for plasmid preparation were also taken at this time (8-hour samples), followed by additional samples being taken every 2 hours, up to 18 hours, then at 24 and 36 hours of post-transformation growth. Purified pSin32 plasmid samples (9 from each strain) were then transformed into MDS42 (McrBC$^-$) and MG1655 (McrBC$^+$). By counting transformed MG1655 and MDS42 colonies for each plasmid sample, the relative number of mutated plasmids could be calculated. To obtain an absolute value for mutated plasmid numbers, each batch of electrocompetent MDS42 and MG1655 indicator strains was transformed with a control (pST76-A) plasmid carrying an Ap resistance cassette. The ratio of MG1655 and MDS42 tansformants was then used as a correcting factor to calculate the absolute values for the number of mutated pSin32 plasmids for each sample.

Figure 5:
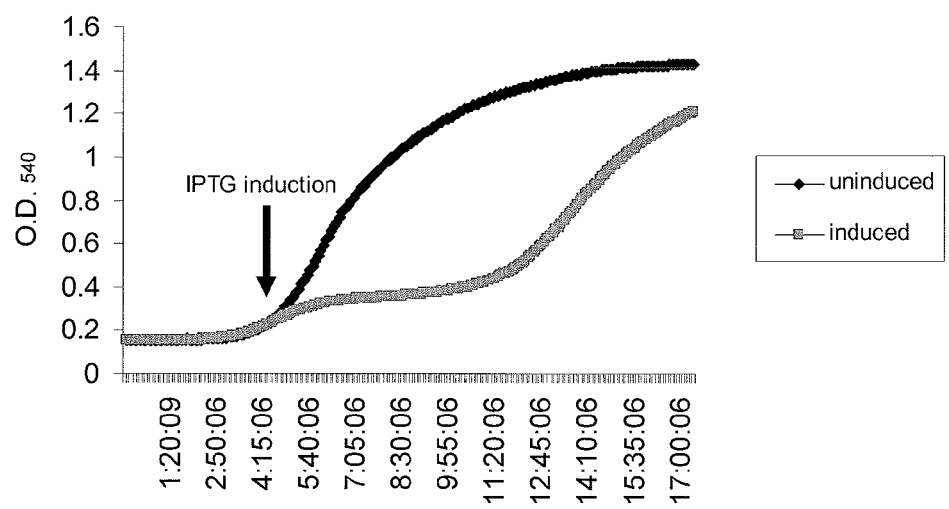
FIG. 5 illustrates the toxic effect of the overproduction of the SinI enzyme on the growth of MDS42-T7 (mcrBC⁻) host. SinI was overproduced from the IPTG-inducible pSin32 plasmid. Both measurements are averages of the O.D.540 values of 25 independent colonies each, measured every 5 minutes using the Bioscreen C automated instrument.
Figure 6:
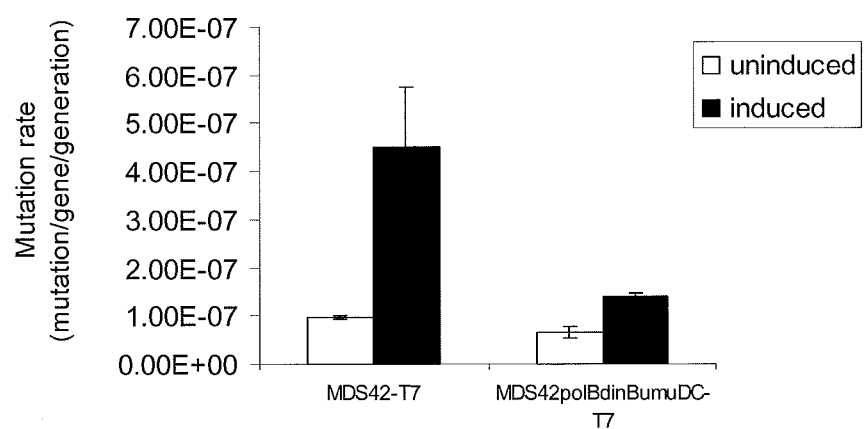
FIG. 6 illustrates the effect of overproduction of SinI methyltransferase on the mutation rate. The SinI methyltransferase enzyme was overproduced from the pSin32 plasmid. Mutation rates were measured using the cycA fluctuation assay. Values are an average of 3 independent measurements each.

Following transformation of BL21(DE3)mcrBC, MDS42-T7 and MDS42polBdinBumuDC-T7 with pSin32, it was found that, upon induction by IPTG, overproduction of the SinI enzyme had a moderate growth-inhibiting effect even in McrBC$^-$ strains (FIG. 5). While this moderate toxicity leads to an elevation in the mutation rate of MDS42-T7, the effect is much weaker in MDS42polBdinBumuDC-T7 (FIG. 6), supporting the findings discussed above.

Figure 7:
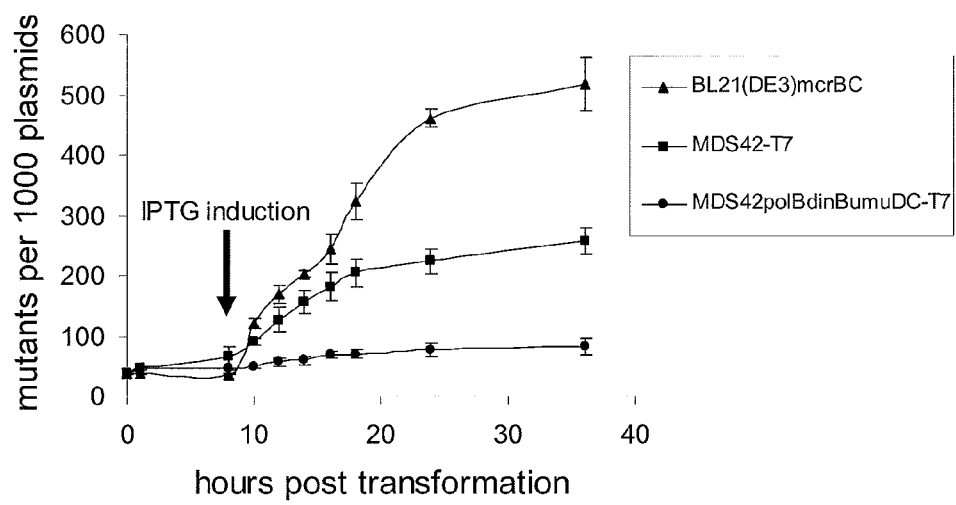
FIG. 7 illustrates the accumulation of plasmids with mutated sinI in various hosts. SinI methyltransferase was expressed from pSin32. Plasmids were isolated at various intervals and screened (by transformation in McrBC$^+$ and McrBC$^-$ hosts) for mutations resulting in a loss of function of the enzyme. Values are averages of 3 independent measurements each.

Following IPTG-induction, plasmid samples were taken at regular intervals. The fraction of the plasmid sample that carried sinI-disabling mutations (unmethylated plasmids) was detected by transforming the plasmid samples back into MG1655 (mcrBC$^+$). The total plasmid number per sample was determined by simultaneously transforming the samples into MDS42. After correcting each value with the transformant number from a control plasmid for each set of electrocompetent cells, the ratio of plasmids coding for functional/non-functional sinI was calculated. The results are illustrated at FIG. 7.

Surprisingly, 96.7% of the starting (0 hour) plasmid sample, originating from MDS42, could not be established in MG1655. This indicated that, even in a host lacking T7 polymerase, spurious transcription of sinI had resulted in SinI expression, and consequently methylation of sinI sites. The methylated status of the SinI sites in the original plasmid sample was confirmed by their uncleavability by SinI.

Differences regarding clone stability in the different strains became evident after IPTG-induction of SinI expression. Thirty-six hours after transformation (28 hours after IPTG-induction), 51.7% of pSin32 harbored in BL21(DE3)mcrBC cells carried mutations preventing the production of active SinI. This value was significantly lower in MDS42-T7 (25.8%). In MDS42polBdinBumuDC-T7, the fraction of mutated pSin32 plasmids was even lower (8.2%). The non-methylated status of the SinI sites on the plasmids carrying a mutated sinI gene was confirmed by their cleavability by SinI.

Figure 8:
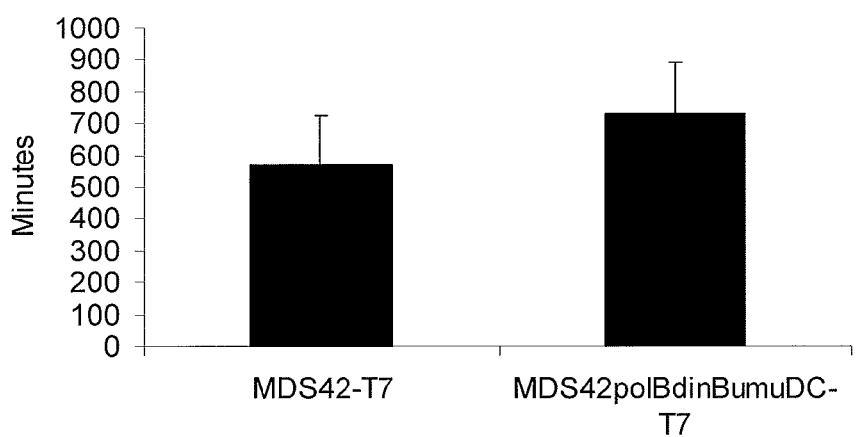
FIG. 8 illustrates the time required to grow to OD=0.7 for cultures of various strains expressing SinI. Growth curves of strains harboring pSin32, induced with IPTG at OD=0.2 (0 min), were measured. OD=0.7 was selected as a cutoff to indicate that a sample had overcome the toxic effect of the overproduced SinI methyltransferase. Values shown are averages of measurements on 50 independent samples of each strain.

The accumulation of mutant plasmids in BL21(DE3)mcrBC and MDS42-T7 was due to a combined effect of stress-induced mutagenesis and growth inhibition by the SinI-expressing plasmid. Overproduction of the enzyme elevated mutation rates and reduced growth. In these slow-growing cultures, over time, SinI-inactivating mutations arose, which then, having resumed their normal growth rate, quickly outgrew the rest of the culture. In low-mutation-rate MDS42polBdinBumuDC-T7, SinI-inactivating mutations developed, on average, over a longer time period. Growth curve measurements of 50 independent colonies of MDS42-T7 and MDS42polBdinBumuDC-T7, all carrying the pSin32 plasmid, support this notion (FIG. 8). An O.D.$_{540}$ value of 0.7 was used as a cutoff to indicate that a culture had overcome the growth-hindering effect of the induced plasmid. The average time taken for MDS42polBdinBumuDC-T7 to reach this level of density was significantly longer than for MDS42-T7 (727.8 and 571.8 minutes, respectively; P<0.005, two-tailed, unpaired t test).

Figure 9:
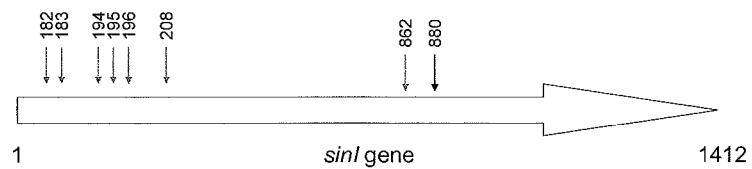
FIG. 9 illustrates mutations in sinI, carried on pSin32 plasmids able to transform MG1655. Eight pSin32 plasmid samples, isolated from McrBC$^+$ host, were sequenced. Seven of them carried frameshift mutations that created new stop codons in sinI (positions 182, 183, 194, 195, 196, 208 and 862). One of the mutations was a A→C transition leading to an Asn→Thr change (position 880). Nucleotide position of each mutation is shown relative to the first nucleotide of sinI.

To verify that mutations had indeed taken place in the plasmids that allowed for growth in McrBC$^+$ cells, the sinI region of 8 different plasmid samples (taken from viable, pSin32-transformed MG1655 colonies) were sequenced (FIG. 9). In seven out of the eight cases, a frameshift mutation had occurred in sinI, resulting in a new stop codon within the gene. The eighth case displayed an A to C transversion, resulting in the N880T mutation of the protein. Six out of the seven new stop codons caused by the frameshifts were located within the first 125 bp of the gene.

These results demonstrate a clear and unexpected practical advantage of reduced genome bacteria having non-functional genes encoding DNA polymerase II, IV and/or V particularly in an IS element-free genetic background. When SinI was overproduced, the sinI gene, carried on a plasmid, acquired loss-of-function mutations approximately three times less frequently in MDS42polBdinBumuDC than in MDS42, and over five times less frequently than in BL21(DE3)mcrBC. Remarkably, after only 16 hours of overproduction in BL21(DE3)mcrBC, nearly half of all sinI genes encoded on the plasmids had suffered a disabling mutation.

The unexpectedly high ratio of mutated clones in the SinI-overexpressing culture cannot be explained solely by the stress-induced mutagenesis, the overall mutation rate of which is too low in absolute values (in the order of $10^{-6}$ mutations/gene/generation) to cause such a dramatic effect. Rather, the phenomenon is in large part due to the growth inhibitory effect of the plasmid carrying the toxic gene. The chain of events is the following: Upon expression of a toxic gene, the growth rate of the cell is reduced. At the same time, mutation rate is increased by the stress. Once a mutant that no longer expresses the toxic function arises in the plasmid population, the cell harboring it can resume normal growth and become dominant in the culture. In reduced genome bacteria having one or more non-functional polB, dinB and/or umuDC genes, as exemplified by MDS42polBdinBumuDC, appearance of such mutants is delayed and the cells can produce the functional toxic product for an extended period of time. The advantage of strains such as MDS42polBdinBumuDC over parent strain MDS42 and the commonly used production strain BL21(DE3) is striking and increases as the severity of the stress of overproducing a product increases. Bacterial strains with high genomic stability as described herein are particularly valuable in therapeutic applications, where fidelity of the nucleic acid and/or protein product is of primary importance. Bacteria of the invention are also surprisingly useful where long-term continuous culture conditions are required.

What is claimed is:

1. A reduced genome *Escherichia coli* bacterium, having a genome that is genetically engineered to be up to 22% smaller than the genome of its native parent strain, wherein said bacterium lacks all IS1, IS2, IS3, IS4, IS5, IS30, IS150, IS186, IS600, IS911 and IS10 insertion sequences and lacks a functional polB gene and lacks a functional dinB gene and optionally lacks a functional umuDC gene, wherein said bacterium has deleted therefrom at least the following DNA segments: b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153 and b2945 of the *E. coli* K-12 strain MG1655.

2. The bacterium of claim 1, wherein the native parent strain of said bacterium is a B strain.

3. The bacterium of claim 2, wherein the native parent strain of said bacterium is strain BL21(DE3).

4. The bacterium of claim 1, wherein the native parent strain of said bacterium is a K12 strain.

5. The bacterium of claim 4, wherein the native parent strain of said bacterium is K12 strain MG1655.

6. The bacterium of claim 5, wherein said bacterium is produced from MDS42 by rendering the polB, dinB and optionally umuDC genes nonfunctional.

7. The bacterium of claim 1, having a functional umuDC gene.

8. The bacterium of claim 1, having a non-functional umuDC gene.

9. The bacterium of claim 1 comprising a heterologous nucleic acid.

10. The bacterium of claim 9 wherein said heterologous nucleic acid comprises a nucleic acid encoding a polypeptide operatively linked to an expression control sequence.

11. A method for producing a polypeptide comprising incubating the bacterium of claim 10 under conditions suitable for expressing the polypeptide and collecting the polypeptide.

12. The bacterium of claim 1 having a non-functional umuDC gene.

13. The bacterium of claim 12 comprising a heterologous nucleic acid, said heterologous nucleic acid comprising a nucleic acid encoding a polypeptide operatively linked to an expression control sequence.

14. A method for producing a polypeptide comprising incubating the bacterium of claim 13 under conditions suitable for expressing the polypeptide and collecting the polypeptide.

15. The bacterium of claim 1, having a genome that is genetically engineered to be up to 20% smaller than the genome of its native parent strain.

* * * * *